United States Patent [19]

Chopin et al.

[11] Patent Number: 5,401,309
[45] Date of Patent: Mar. 28, 1995

[54] RARE EARTH METAL SULFIDE PIGMENT COMPOSITIONS

[75] Inventors: Thierry Chopin, Saint Denis; Dominique Dupuis, Deuil-La-Barre, both of France

[73] Assignee: Rhone-Poulenc Chimie, Courbevoie Cedex, France

[21] Appl. No.: 229,404

[22] Filed: Apr. 18, 1994

[30] Foreign Application Priority Data

Apr. 16, 1993 [FR] France ................................. 93 04544

[51] Int. Cl.$^6$ ............................................. C09C 1/02
[52] U.S. Cl. ................................... 106/461; 106/403; 106/404; 106/437; 106/439; 106/450; 106/451; 106/482; 423/263
[58] Field of Search ............... 106/403, 404, 437, 439, 106/450, 451, 461, 482; 423/263, 265

[56] References Cited

U.S. PATENT DOCUMENTS

| | | | |
|---|---|---|---|
| 4,545,967 | 10/1985 | Reynolds et al. | 423/263 |
| 4,765,931 | 8/1988 | Saunders et al. | 252/584 |
| 5,348,581 | 9/1994 | Chopin et al. | 423/263 |

FOREIGN PATENT DOCUMENTS

0203838A3  12/1988  European Pat. Off. .

*Primary Examiner*—Helene Klemanski
*Attorney, Agent, or Firm*—Burns, Doane, Swecker & Mathis

[57] ABSTRACT

Novel colorant/pigment compositions, prepared via precipitation technique and well suited for the coloration of a wide variety of materials and substrates, e.g., plastics, paints and inks, ceramics, cosmetics, etc., comprise composite core/sheath particulates, the cores of which comprising particles of at least one crystalline rare earth metal sesquisulfide having the formula $M_2S_3$ in which M is at least one lanthanide element having an atomic number of from 57 to 71, or yttrium, and such core particles having at least one alkali and/or alkaline earth metal dopant at least in part incorporated within the crystal lattice of the at least one crystalline rare earth metal sesquisulfide, and each sheath comprising a coating layer of at least one transparent oxide deposited onto the external face surfaces of the doped core particles.

41 Claims, No Drawings

RARE EARTH METAL SULFIDE PIGMENT COMPOSITIONS

BACKGROUND OF THE INVENTION

1. Field of the Invention

The present invention relates to novel inorganic pigment compositions based on the rare earth metal sulfides, and, more especially, to novel pigment compositions comprising specific rare earth metal sesquisulfides and transparent oxides in the form of particles of core-/shell type, the sulfides constituting the core and the transparent oxides the shell or sheath coating therefor.

The present invention also relates to a process for the preparation of such novel compositions and to the use thereof for the coloration of various materials and substrates.

2. Description of the Prior Art

Inorganic colorants/pigments are currently widely used in numerous industries, especially in the paints, plastics and ceramics industries. For such applications, their various properties, notably intrinsic color, coloring power and opacifying power, thermal stability, chemical stability, dispersibility (ability of a product to disperse properly in a given medium), and the absence of toxicity, constitute particularly important criteria to be taken account of in the selection of a suitable pigment.

The rare earth metal sesquisulfides, of general formula $M_2S_3$ in which M represents at least one rare earth metal, are known compounds and have been described in numerous publications.

Moreover, their use as colorants/pigments for the coloration of various materials, such as, for example, plastics, paints and others, is described, in particular, in EP-A-0,203,838, assigned to the assignee hereof and hereby expressly incorporated by reference.

However, for this application, it transpires that the rare earth metal sesquisulfides hitherto known to this art display characteristics, especially chromatic characteristics, as well as a stability, both thermal and chemical, which remain insufficient and militate against any meaningful development thereof.

Another difficulty is presented by the fact that most of the synthesis processes for preparing rare earth metal sesquisulfides of high phase purity entail reactions of the solid (rare earth metal compounds such as oxides)/gas (sulfurizing agents such as $H_2S$) type under pressure and/or temperature conditions which are incompatible with operation on an industrial scale. In addition, certain parasitic phases are typically formed consisting especially of rare earth metal oxysulfides which may mask or degrade the intrinsic color of the desired pure sesquisulfides.

SUMMARY OF THE INVENTION

Accordingly, a major object of the present invention is the provision of a novel class of inorganic colorant compositions which present, among other advantages, chromatic characteristics which are surprising and unexpected, improved chemical and thermal stability and an absence of toxicity, the subject compositions being well suited for the coloration of numerous materials and substrates.

Another object of the present invention is the provision of a process for the preparation of such novel compositions that is simple, economic, reproducible, controllable and compatible with production on an industrial scale.

Briefly, the present invention features novel inorganic colorant/pigment compositions comprising (a) a support (or core, or nucleus) of at least one rare earth metal sesquisulfide of formula $M_2S_3$ in which M is at least one element selected from among the lanthanides of atomic number ranging from 57 to 71, inclusive, and yttrium, said support also containing at least one alkali metal and/or alkaline earth metal element, at least a fraction of which being included within the crystal lattice of said rare earth metal sesquisulfide, and (b) a coating layer (or shell, or envelope) of at least one transparent oxide deposited onto the external face surface of said support.

DETAILED DESCRIPTION OF BEST MODE AND PREFERRED EMBODIMENTS OF THE INVENTION

More particularly according to the present invention, it has now been found that the subject novel compositions are well suited as colorants/pigments due to their numerous and very advantageous properties, such as, notably, a very wide range of excellent intrinsic colors, a very good coloring power, a very good opacifying power, a very good dispersibility, particularly in plastics, a very good thermal stability at temperatures of up to 500° C., and a very good chemical stability in media such as water (at neutral, basic or weakly acidic pH) and organic solvents.

As indicated above, the constituent supports of the compositions according to the invention contain one or more alkali metals, one or more alkaline earth metals, or, alternatively, mixtures of alkali metal(s) and alkaline earth metal(s).

Also, in the description which follows, the expression "doping element" or "dopant" is used, for simplicity, to denote both an alkali metal and an alkaline earth metal, as well as any combination of alkali metal(s) and/or alkaline earth metal(s).

Moreover, by the term "rare earth metal(s)" is intended, either singly or in combination, the elements of the lanthanide series of the Periodic Table having an atomic number from 57 to 71, inclusive, as well as yttrium of atomic number 39.

The process for the synthesis of the colorant/pigment compositions according to the invention comprises the following essential steps:

(i) contacting an inorganic support as described above with a precursor of the desired transparent oxide,
(ii) precipitating the transparent oxide thereon, and
(iii) separating the composition obtained from the medium of reaction.

Overall, the process according to the invention is based on the principle of a chemical precipitation of a transparent oxide precursor, conducted "in situ" in a medium comprising a dispersion (or suspension) of particles of the aforementioned inorganic support, said precipitated oxide then being deposited onto the external face surface of each of the particles which comprise said inorganic support.

Thus, composite particles (or pigments) are directly formed, corresponding to the original support, but in a form perfectly encapsulated by an external protective layer, of controlled thickness, of the transparent oxide.

The process according to the present invention presents, among others, the advantage of not altering, or altering only very slightly, on the one hand, the size of the particles constituting the particulate support starting material before coating, as well as, on the other, the excellent intrinsic chromatic characteristics associated with these particles. It is even possible for said characteristics to be substantially improved. In addition, the shell or sheath thus constituted at the surface of said initial particles provides compositions having markedly improved thermal and chemical stability.

Lastly, the present invention also features colorants/pigments comprising the compositions described above.

The novel compositions according to the invention will now be more fully described.

A first essential characteristic of the compositions based on rare earth metal sesquisulfides according to the invention is in their specific structure or morphology.

As indicated above, this structure may be described in the following manner: the composition according to the invention comprises an inorganic support particle which defines a nucleus or core and, coating this nucleus or core, a peripheral outer layer of a transparent oxide.

It will of course be appreciated that certain variants of this structure are permissible. In particular, the peripheral layer coating the particle does not have to be perfectly continuous or homogeneous. However, the compositions according to the invention preferably comprise a coating layer of transparent oxide which is uniform and of controlled thickness, and this in a manner such as not to alter the original color of the support prior to coating.

A second essential characteristic of the compositions based on rare earth metal sesquisulfides according to the invention is in their specific composition, and this as much with regard to the inorganic support itself as to the protective layer coating same.

Thus, the first specific constituent element of the compositions based on rare earth metal sesquisulfides according to the invention is the transparent oxide deposited onto the surface of the support. By "transparent oxide" is intended an oxide which, once deposited onto a support in the form of a more or less thin film absorbs few or no light rays in the visible region, and this in a manner such as to mask little or none of the original intrinsic color of the support. In addition, it should also be appreciated that the term oxide, which is used for convenience throughout the present description, also comprehends the oxides of hydrated type.

These oxides, or hydrated oxides, may be amorphous and/or crystallized.

Exemplary such oxides include, in particular, silicon oxide (silica), aluminum oxide (alumina), zirconium oxide (zirconia), titanium oxide, zirconium silicate $ZrSiO_4$ (zircon) and the rare earth metal oxides. Among these, it is preferred to use those which have no officially recognized toxicity to man and/or the environment.

In a preferred embodiment of the compositions of the present invention, the coating layer is based on silica. Even more advantageously, this layer essentially, and preferably exclusively, consists of silica.

Next, the second specific constituent element of the compositions based on rare earth metal sesquisulfides according to the invention is the inorganic support based on rare earth metal sesquisulfides doped with one or more alkali metal and/or alkaline earth metal elements. As will be more fully described below, such a support, prior to its coating, itself constitutes a colored inorganic pigment with which numerous advantageous properties are associated. Said colored inorganic support essentially determines and conditions the final coloration of the composition or of the colored composite pigment of the present invention. Stated differently, to obtain a composition or a composite pigment in accordance with this invention having a given color requires employing a support having this same color. The peripheral transparent oxide layer makes it possible not to alter, or to barely alter, the original color of the support, while at the same time enhancing the thermal and/or chemical resistance of the latter.

The doping element may be present in different forms in the support.

However, it is essentially preferably present in a combined form with the rare earth sesquisulfides. In this case, the doping element is then irreversibly associated with the sesquisulfides, in the sense that, for example, even very rigorous washes of the latter do not remove the dopant. Such washes can, to the contrary, effect removal of the optional sulfides and/or polysulfides of alkali metal(s) or alkaline earth metal(s) present at the surface of the supports (before coating) and, thus, not irreversibly associated with the latter.

Without wishing to be bound by or to any particular theory, the following explanation is probable:

It is known that rare earth metal sesquisulfides $M_2S_3$ crystallize into a crystallographic structure of $Th_3P_4$ type, which has lacunae in the cation lattice. This lacunar structure may be symbolized by giving the sesquisulfides the formula $M_{10.66}\{\}_{1.33}S_{16}$ (see, in particular on this subject, W. H. ZACHARIASEN, "Crystal Chemical Studies of the 5f-Series of Elements. The $Ce_2S_3$–$Ce_3S_4$ Type of Structure", Acta Cryst., 2, 57 (1949)).

According to the invention, alkali metal and/or alkaline earth metal elements may be introduced into these cationic lacunae, to the point of saturation or otherwise of the latter. The presence of the doping element within the supports of the invention may be demonstrated by simple chemical analysis. Moreover, X-ray diffraction analyses evidence that there is conservation of the sesquisulfide $Th_3P_4$ crystalline phase with, in certain cases, a more or less considerable modification of the lattice constants, which is a function both of the nature and of the amount of doping element introduced.

Thus, it has unexpectedly and surprisingly now been determined that this insertion into the sesquisulfide crystal lattice imparts chromatic characteristics which are clearly improved relative to all of the rare earth metal sesquisulfides hitherto known to this art. In addition, the presence of the dopant may elicit the beneficial effect of stabilizing at high temperatures the crystalline structure of the particular sesquisulfide and, therefore, of conserving the desired color over a wider temperature range.

In a preferred embodiment of the compositions according to the invention, the doping element present in the support is an alkali metal element and is selected, for example, whether alone or in combination, from among lithium, sodium, and potassium.

Even more preferably, the alkali metal is sodium.

Exemplary alkaline earth metal dopants according to the invention include magnesium, calcium, barium and strontium.

In another preferred characteristic of the subject compositions, the molar amount of alkali metal(s) and/or alkaline earth metal(s) present in the support is at least equal to 0.1%, and advantageously ranges from 5% to 50% of the molar amount of rare earth metal(s) present in this support.

The nature of the rare earth metal(s), as well as the type of crystal lattice of the sesquisulfide, are selected as a function of the color sought to be obtained for the composition or the pigment. In all cases, it is observed that, for a suitably selected doping element, the compositions according to the invention then have much more intense colorations than those of the corresponding sesquisulfides which are not doped with an alkali metal and/or alkaline earth metal element. By "corresponding sesquisulfide" is intended the sesquisulfide containing the same rare earth metal(s) and having the same crystallographic habit.

For a given rare earth metal sesquisulfide, and hence of given coloration, the invention thus provides, after simple routine tests, an entire range of compositions of improved colors, simply by manipulating the nature and/or the concentration of the doping element in the support.

Examples of colors which may be provided via the compositions of the invention are given below, as a function of the nature of the support:

(1) the compositions for which the support is based on cerium sulfides have a color varying from brown to red according to the conditions for the preparation thereof, in particular the calcination temperature. They are brown or blood-red depending on whether they have the orthorhombic b-$Ce_2S_3$ phase (J.C.P.D.S. 20 269) or the cubic $\gamma$-$Ce_2S_3$ phase (J.C.P.D.S. 27 104);

(2) with lanthanum, yellow compositions are obtained, with a cubic $La_2S_3$ structure (J.C.P.D.S. 25 1041);

(3) a green coloration may be obtained with neodymium, and a green-yellow coloration with praseodymium. The supports then have the cubic $Nd_2S_3$ structure (J.C.P.D.S. 26 1450) and the cubic $Pr_2S_3$ structure (J.C.P.D.S. 27 481), respectively;

(4) a yellow-brown pigment is available with dysprosium of cubic $Dy_2S_3$ structure (J.C.P.D.S. 26 594);

(5) compositions having various shades of brown may also be obtained: ochre with terbium of cubic $Tb_2S_3$ structure, brown with erbium of monoclinic $Er_2S_3$ structure (J.C.P.D.S. 21 324) and dark beige with yttrium of monoclinic $Y_2S_3$ structure (J.C.P.D.S. 22 996);

(6) finally, other examples of colors which may be obtained are: brown-grey with samarium of cubic $Sm_2S_3$ structure (J.C.P.D.S. 26 1480), brown-green with gadolinium of cubic $\gamma$-$Gd_2S_3$ structure (J.C.P.D.S. 26 1424), and green-gold with thulium of monoclinic $Tm_2S_3$ structure (J.C.P.D.S. 30 1364).

The intrinsic coloration of both the pigment supports and of the compositions according to the invention may, moreover, be quantified by means of the chromatic coordinates $L^*$, $a^*$ and $b^*$ given in the CIE 1976 system ($L^*$, $a^*$, $b^*$) as defined by the Commission Internationale d'Eclairage and itemized in the Recueil ds Normes Francaises (AFNOR), colorimetric color No. X08-12 (1983). They are determined using a colorimeter marketed by Pacific Scientific. The nature of the illuminant is D65. The observation surface is a circular pellet of surface 12.5 cm². The observation conditions correspond to viewing under an aperture angle of 10°. In the measurements reported the reflective component is excluded.

$L^*$ provides a measurement of the reflectance (light-/dark shade) and varies accordingly from 100 (white) to 0 (black). $a^*$ and $b^*$ are the values of the color tendencies:

$a^*$ positive=red
$a^*$ negative=green
$b^*$ positive=yellow
$b^*$ negative=blue $L^*$ thus represents the variation from black to white, $a^*$ the variation from green to red and $b^*$ the variation from blue to yellow.

Thus, according to the present invention, and strictly by way of example, when the rare earth metal is cerium and the sesquisulfide is in the cubic $\gamma$ crystallographic form, the compositions or pigments have the following remarkable trichromatic coordinates:

$L^*$ at least equal to 30, and especially ranging from 30 to 60;

$a^*$ at least equal to 30, and especially ranging from 35 to 65;

$b^*$ generally ranges from 0 to 40.

Such coordinates, and in particular the $a^*$ chromatic coordinate, correspond to an intense red color which is notably exceptional for a cubic $\gamma$-$Ce_2S_3$ cerium sulfide, and equivalent to or even greater than that of the red reference pigments, namely cadmium selenide and cadmium sulfoselenide. In addition, one of the advantages of such a pigment is that it displays none of the toxicity problems associated with the presence of heavy metals, as is generally the case in the pigments of the prior art.

As indicated above, the present invention also features an industrial manufacturing process for the preparation of the subject novel compositions. However, before elucidating the parameters thereof, the details of a particularly advantageous process for the synthesis of sesquisulfides doped by alkali metals and/or alkaline earth metals which are used as the support substrates will first be given, such supports constituting one of the essential starting materials for the preparation of the compositions according to the invention. It will be appreciated that the process which follows is particularly suitable for preparing support compositions in which the rare earth metal sesquisulfide is present in the cubic, and especially cubic $\gamma$, crystal habit.

This process entails producing an initial mixture containing at least one rare earth metal compound, sulfur and at least one compound of an alkali metal and/or alkaline earth metal element (doping element), heating said initial mixture until the desired sesquisulfide phase is obtained, under an atmosphere which is non-oxidizing, preferably reducing, and then cooling the mixture thus treated.

In a preferred embodiment of this process, heating of the initial mixture is carried out in the presence of a reducing agent. The amount of reducing agent added is then determined such as to maintain a very low partial pressure of oxygen in the reactor. Thus, the amount of reducing agent used is advantageously sufficient to consume the free and/or combined oxygen contained in the initial mixture.

In a variant of this embodiment, a reducing agent is added directly to the initial mixture. This agent is generally based on carbon, such as, for example, graphite, coke, lignite or, alternatively, an organic compound which generates carbon on heating. This may also be a metallic reducing agent, for example aluminum.

In a second such variant, the reducing agent is contained in the gas which forms the non-oxidizing atmosphere. The initial mixture is then advantageously flushed with a non-oxidizing gas, preferably an inert gas, containing a reducing agent such as, for example, hydrogen or carbon monoxide CO. A mixture of hydrogen with an inert gas, such as an argon/hydrogen or nitrogen/hydrogen mixture, or, alternatively, an argon/CO or nitrogen/CO mixture, can thus be used. This flushing may also be carried out using hydrogen or carbon monoxide individually.

During the temperature increase, the mixture is advantageously maintained at an intermediate temperature, especially ranging from 250° C. to 500° C., before adjusting the mixture to the temperature corresponding to the formation of the desired sesquisulfide. Maintenance of this intermediate temperature is carried out for a period of time generally ranging from 15 minutes to 1 hour.

The rare earth metal compounds which are suitable for the above process are, for example, selected from among rare earth metal oxycarbonated compounds, sulfates and rare earth metal oxides. Particularly exemplary rare earth metal oxycarbonated compounds are rare earth metal carbonates, oxalates, acetates, malonates and tartrates.

As regards the alkali metal or alkaline earth metal compounds, exemplary thereof are the oxides, sulfides or polysulfides, sulfates, oxycarbonated compounds such as oxalates, carbonates or acetates, of alkali metals or alkaline earth metals. The carbonates of these elements are the preferred.

The amount of alkali metal or alkaline earth metal element added is determined in order to provide a molar ratio: doping element/rare earth metal(s) generally ranging from 0.05 to 0.5, and preferably from 0.15 to 0.30 in the initial mixture.

Moreover, the amount of sulfur present in the initial mixture is determined in order to provide a molar ratio: sulfur/rare earth metal(s) greater than or equal to 1.5 and preferably greater than 2.

The sulfur may be introduced in free state (solid or gaseous elemental sulfur) or in the form of a sulfurized precursor compound, for example $Na_2S$ or $CS_2$.

Elemental sulfur in the solid state is preferably used°

The initial mixture may, of course, comprise several rare earth metal and/or alkali metal and/or alkaline earth metal compounds, as indicated above.

The initial mixture thus obtained is subsequently heated at a temperature and for a period of time which are sufficient to produce the desired sesquisulfide phase, this time generally being proportionally shorter as the temperature is increased.

This temperature depends, of course, on the particular sesquisulfide under consideration.

The mixture is advantageously heated at a temperature greater than 900° C. generally ranging from 1,000° C. to 1,400° C., preferably 1,150°–1,300° C., and for at least 30 minutes, preferably from 30 minutes to two hours.

The product thus obtained may subsequently be optionally subjected to one or more washes, for example with water, in order to decrease the content of non-bound alkali metal(s) and/or alkaline earth metal(s).

If necessary, the product obtained may lastly be ground (grinding with an air jet or other) in order to provide an average particle diameter ranging from 0.2 $\mu$m to 5 $\mu$m. However, this particle size is generally obtained without having to grind the product, which presents a very considerable advantage from an economic point of view.

The product obtained then has a very good phase purity (especially absence of oxysulfide) and outstandingly increased chromatic coordinates in the specific color of the rare earth metal sesquisulfide under consideration.

As indicated above, these products (doped rare earth metal sesquisulfides) are destined to constitute the support of the colorant/pigment compositions according to the present invention.

The process for the preparation of these colorants of core/shell type will now be more fully described.

This process essentially entails the precipitation of a transparent oxide, which forms a protective layer, at the surface of a support as described above. The principle for the preparation of the novel compositions according to the invention thus essentially comprises intimately contacting the inorganic particle or support to be treated and a precursor of the layer-forming oxide, and in precipitating this oxide.

It will of course be appreciated that the invention is not limited to any specific preparative technique. In addition, for best operation of the subject processes, it is desirable as far as is possible to avoid the contact, before or during the precipitation step, of the rare earth metal sesquisulfide supports with a medium which is too acidic, which could initiate the decomposition of said sesquisulfides.

This process will first be described in the specific and preferred embodiment where the layer-forming oxide is silica.

This process may essentially be carried out according to two variants.

In the first variant, which is the preferred, the process essentially comprises preparing the silica by hydrolysis of an alkyl silicate.

More particularly, the support and an alkyl silicate are intimately admixed, the alkyl silicate being hydrolyzed, and the pigment formed and the liquid phase of the reaction medium are separated.

It will be appreciated that the principle of this technique is more particularly described in STÖBER et al, *Journal of Colloid and Interface Science*, 26, pp. 62–69 (1969).

Generally, it is preferable to carry out the hydrolysis in the presence of a base which then serves as a catalyst.

A reaction medium is formed by mixing water, alcohol, the support which is then in suspension, and optionally a base, and by subsequently introducing the alkyl silicate. The reaction is preferably conducted with stirring.

It is preferred to use aqueous ammonia as the base. The alcohols employed are generally aliphatic alcohols such as butanol. The alkyl silicate is preferably introduced with an alcohol.

Although the reaction can be conducted at room temperature, a substantial improvement in the quality of the coating layer is, however, attained when the hydrolysis temperature is greater than room temperature, in particular ranging from 40° C. to 70° C.

It is also possible to formulate an initial charge based on alcohol and alkyl silicate, and to subsequently introduce water or a water/base mixture thereto.

Ethyl silicate may, in particular, be used as the alkyl silicate.

After reaction and precipitation, the pigment obtained is separated from the reaction medium by any technique per se known to this art, in particular by centrifugation or filtration, and is generally subsequently washed with alcohol and then dried.

As regards the second variant, the process comprises intimately contacting, mixing and reacting the support, a silicate and an acid, whereby silica is precipitated.

In a first embodiment of this second variant, the acid and silicate are added simultaneously to the reaction medium. More particularly, an aqueous suspension of the support is first formed, and subsequently the acid and an aqueous silicate solution are added simultaneously to the reaction medium.

In a specific embodiment, the acid and silicate may then be introduced, while maintaining the pH of the reaction medium constant. This pH is generally fixed at a value ranging from 8 to 9.

The reaction temperature may vary widely. This temperature generally ranges from 60° to 100° C.

A second embodiment (preferred to the first) of this second variant of the process according to the invention comprises first forming a suspension of the support in an aqueous silicate solution, and subsequently introducing the acid into the suspension thus formed. In this case, the pH of the precipitation medium is advantageously set at a value greater than 7, and preferably greater than 8, such as to avoid a harmful dissolution of the support based on the rare earth metal sulfides.

In this second variant, the temperature conditions are identical to those described in the first.

Regarding the silicate, an alkali metal silicate is generally used and, more particularly, the silicates of sodium, potassium or lithium.

In respect of the acids, an acid selected from among sulfuric, nitric, hydrochloric and carbonic acids is advantageously used. The acid is generally employed in the form of an aqueous solution.

The separation between the pigment, on the one hand, and the liquid phase of the reaction medium, on the other, which are obtained according to the processes described above, is subsequently effected in a manner known per se, for example by filtration. The separated pigment is subsequently dried.

In the event that the layer-forming oxide is alumina, several embodiments are acceptable.

In a first embodiment, the support, an aluminate and an acid are intimately contacted and reacted, whereby alumina is precipitated.

In one variant of this embodiment, the aluminate and the acid may be simultaneously introduced into an aqueous suspension of the support. In this case, the operation may be carried out such as to maintain the pH of the reaction medium constant, this pH preferably being greater than 7 and even more preferably greater than 8.

In a second variant of this embodiment, a suspension of the support is first formed in an aluminate solution and the acid is then introduced into this suspension. Here also, the pH of the reaction medium during introduction of the acid will be monitored such that it preferably remains greater than 7, or even greater than 8.

An alkali metal aluminate is generally employed in this first embodiment. Exemplary of the acids are hydrochloric or nitric acid.

The second embodiment for the preparation of a composite pigment according to the invention with alumina as the layer-forming oxide comprises intimately contacting, mixing and reacting the support, an aluminum salt and a base, whereby alumina is precipitated.

It may thus entail, for example, using an initial charge comprising an aqueous suspension of the support and then simultaneously introducing the base and the aluminum salt into this suspension.

The base is generally sodium hydroxide or aqueous ammonia, and the aluminum salt may, for example, be an aluminum halide such as aluminum chloride, or, alternatively, aluminum nitrate.

Lastly, according to a third embodiment, the compositions may be prepared with the layer-forming alumina by obtaining said alumina by hydrolysis of an aluminum alcoholate.

This embodiment is related to that described above for the hydrolysis of an alkyl silicate.

The process is then carried out by intimately contacting the support and an aluminum alcoholate; this alcoholate is hydrolyzed, and the pigment formed and the liquid phase of the reaction medium are separated.

That which has been described above in the context of the hydrolysis of an alkyl silicate applies here by analogy, especially regarding the use of a base and the technique of introduction of the reactants.

Aluminum methylate, ethylate isopropylate or butylate are exemplary aluminum alcoholates, these alcoholates being in liquid form or solid form dispersed or dissolved in an organic solvent, for example benzene or the corresponding alcohol.

In the case of the preparation of a composite pigment comprising titanium dioxide as the layer-forming oxide, various techniques are possible.

The first comprises producing a precipitate of $TiO_2$ by introducing, on the one hand, a titanium salt such as $TiCl_4$, $TiOCl_2$ or $TiOSO_4$ and, on the other, a base such as sodium hydroxide or aqueous ammonia, into an aqueous suspension of the support. The introduction of the salt and the base is carried out simultaneously. A maturation or aging of the pigment may subsequently be performed.

A second method comprises hydrolyzing an alkyl titanate, for example isopropyl titanate. This method is of the same type as that described above for the hydrolysis of an alkyl silicate. The procedure is thus carried out by intimately contacting the support and an alkyl titanate. The alkyl titanate is then hydrolyzed, and the pigment formed and the liquid phase of the medium are separated. That which has been described above in respect of the mode of introduction of the reactants applies here equally as well.

For the preparation of compositions comprising zirconium oxide as the layer-forming oxide, the preparative techniques are of the same type as those described above for titanium dioxide, namely, precipitation by reacting a zirconium salt with a base, or hydrolysis of an alkyl zirconate.

Similarly, for the preparation of compositions comprising one or more rare earth metal oxides as the layer-forming oxide, the procedure may be carried out either by hydrolysis of a rare earth metal alcoholate or by precipitation, by simultaneously introducing, on the one hand, a rare earth metal salt (nitrate or chloride) and, on the other, a base (for example sodium hydroxide or aqueous ammonia) into an aqueous suspension of the support.

Lastly, in the case of zircon defining a coating layer around the support, the procedure can be carried out in the following manner: a zirconium alcoholate and a silicon alcoholate are hydrolyzed together in an aqueous suspension of the support, in the presence of sodium fluoride NaF, the pigment thus formed is recovered and this pigment is then calcined to convert the precipitated coating layer into a zircon phase, NaF then serving as a flux which assists said conversion at the lowest possible temperature.

It will be appreciated that, in general, it remains within the scope of the present invention to prepare compositions having either several oxides forming several successive layers, or mixtures of oxides or mixed oxides forming a single layer.

In addition, the options of carrying out one or more pretreatments of the support (before coating) to further improve certain of its characteristics or properties over the course of the coating treatment, or even to improve certain of the characteristics or properties of the resulting composite pigment, are also available.

The particle size of the compositions recovered is fine and regular, and may range from 1 to 5 microns. With such a particle size, the products may be use directly as pigments, especially for plastics. As indicated above, this particle size is in direct relation with the initial particle size of the support particles used in the coating process according to the invention. This initial particle size must thus be selected in accordance with and with allowance made for the particle size desired for the final composite pigment with a view to a given specific application.

Other than their excellent intrinsic colors and their improved chemical and/or thermal stability, the compositions according to the invention have a very good coloring power and a very good opacifying power. By these facts, they are perfectly suited for the coloration of numerous materials and substrates, such as plastics, paints and others. They may thus themselves constitute colored pigments, or may be formulated into compositions of colored pigments. In this regard, the polyvalence of the compositions according to the invention presents one of their great advantages.

Thus, more particularly, the compositions or pigments of the invention may be used for the coloration of plastics which may be of the thermoplastic or thermosetting type.

Exemplary thermoplastic resins or plastics that are conveniently colored according to the invention include, in particular, polyvinyl chloride, polyvinyl alcohol, polystyrene, styrene/butadiene, styrene/acrylonitrile and acrylonitrile/butadiene/styrene (A.B.S.) copolymers, acrylic polymers, in particular polymethyl methacrylate, polyolefins such as polyethylene, polypropylene, polybutene and polymethylpenetene, cellulose derivatives such as, for example, cellulose acetate, cellulose acetobutyrate and ethyl cellulose, and polyamides such as nylon 66.

Exemplary thermosetting resins or plastics for which the compositions or pigments according to the invention are also suitable include, in particular, the thermosetting phenolic resins, amino resins, especially urea-/formaldehyde and melamine/formaldehyde copolymers, epoxy resins and polyesters.

The compositions or pigments of the invention may also be incorporated into special polymers such as fluorine-containing polymers, in particular polytetrafluoroethylene (P.T.F.E.), polycarbonates, silicone elastomers and polyimides.

In this specific application for the coloration of plastics, the compositions or pigments of the invention may be used directly, in the form of powders. Preferably, they may also be used in a predispersed form, for example premixed with a part of the resin, in the form of a paste concentrate or a liquid, which makes it possible to introduce them at any stage in the manufacture of the resin. This latter attribute constitutes a particularly important advantage of the compositions according to the invention.

Thus, the colorants of the invention may be incorporated into plastics such as those indicated above in a weight proportion ranging generally either from 0.01% to 5% (relative to the final product) or from 40% to 70% in the case of a concentrate.

The products of the invention may also be used in the field of paints and clear varnishes and, more particularly, in the following resins: alkyd resins, the most typical of which are the glycerophthalic resins; long or short oil-modified resins; acrylic resins, prepared from esters of acrylic acid (methyl or ethyl) and methacrylic acid, which are optionally copolymerized with ethyl, 2-ethylhexyl or butyl acrylate; vinyl resins such as, for example, polyvinyl acetate, polyvinyl chloride, polyvinyl butyral and polyvinyl formal, and copolymers of vinyl chloride and vinyl acetate or vinylidene chloride; amino or phenolic resins which are typically modified; polyester resins; polyurethane resins; epoxy resins; silicone resins; etc.

The compositions or pigments are generally incorporated in a proportion of 5% to 30% by weight of the clear varnish.

Finally, the products according to the invention may also be suitable for applications in the rubber industry, especially for floor coverings, in the paper and printing inks industry, in the field of cosmetics, and numerous other uses such as, for example, and without limitation, leather finishing and laminated coverings for kitchen and other work surfaces, and ceramics.

More particularly in respect of the cosmetics, the compositions or pigments of the invention may be formulated into nail polishes and varnishes and in makeup products such as lipsticks, dry make-ups, greasy make-ups or foundations.

They may thus be used in nail polishes/varnishes which generally contain:
(a) a film-forming agent based on nitrocellulose,
(b) a resin, natural dammer resin or synthetic resin of the formaldehyde/sulfamide type, polystyrene resin, polyvinyl resin, and the like,
(c) a plasticizer, for example diethyl phthalate, dibutyl phthalate, dioctyl phthalate, tricresyl phosphate, n-butyl stearate, resorcinol diacetate or mixture thereof,
(d) a solvent such as ethyl, isopropyl, butyl or isobutyl alcohol, ethyl acetate, butyl acetate or, most usually, a mixture of these solvents,
(e) a diluent, especially toluene or xylene, and
(f) other optional additives, perfumed or nacreous product (mica flakes coated with bismuth oxychloride or titanium dioxide).

One example of a typical such composition is as follows:
(i) from 10% to 15% by weight of nitrocellulose,
(ii) from 10% to 15% by weight of resin,
(iii) from 3% to 5% by weight of plasticizer(s),
(iv) from 3% to 5% by weight of pigment(s),
(v) q.s. for 100% by weight of solvent(s).

The compositions or pigments are typically ground in a plastic mass comprising nitrocellulose and plasticizer(s), which is subsequently dissolved in the solvent(s).

Another application of the compositions or pigments of the invention is for inclusion in lipsticks.

The compositions or pigments are typically incorporated in a weight concentration of 5% to 15% expressed relative to the total weight of a formulation which contains:
- (a) an excipient formed from a mixture of various materials to provide the desired consistency: beeswax, carnauba wax, ozocerites, paraffin, synthetic waxes or mixture thereof and a soft excipient which permits adjusting the consistency, such as cocoa butter, petrolatum and hydrogenated white oils, for example palm, ground nut or castor oil,
- (b) various additives, in particular a perfume or aroma and isopropyl myristate or isopropyl palmitate, which imparts a slippery consistency,
- (c) an intermediary solvent for suspending the pigment in the lipophilic phase, which may be castor oil or a glycol such as polyoxyethylene glycol 400 or fatty acid esters: propylene glycol monoricinoleate, isopropyl myristate, isopropyl palmitate or butyl stearate.

The eye make-ups and rouges may be in the form of dry make-ups or greasy make-ups. The content of the subject compositions or pigments in such make-ups may vary over wide limits, for example from 5% to 20%.

The dry make-ups are powders (talc, magnesium carbonate or zinc stearate) which are filled with pigments and agglomerated either with methyl cellulose or with stearates.

One composition of an eyeshadow is as follows:

| | | |
|---|---|---|
| (i) | magnesium aluminum silicate (Veegum F) | 7% by weight |
| (ii) | talc | 50% by weight |
| (iii) | zinc oxide | 4% by weight |
| (iv) | zinc stearate | 11% by weight |
| (v) | kaolin | 10% by weight |
| (vi) | pigment | 18% by weight |

The compositions or pigments of the invention may also be employed in foundation formulations.

Foundations are characteristically in the form of an emulsion, generally of the oil-in-water type.

The lipophilic phase most often comprises:
- (a) an oily component such as liquid paraffin, esters of fatty acids and optionally fatty alcohols, for example oleyl oleate, decyl oleate, octyl stearate, di-n-butyl adipate, isopropyl myristate, isopropyl palmitate, isopropyl stearate, esters of capric and caprylic acids with saturated fatty alcohols having from 12 to 18 carbon atoms, a silicone oil or mixture thereof,
- (b) an emulsifying agent of the anionic and/or nonionic type and more preferably fatty acid salts, sodium stearate, potassium or ammonium stearate and sodium palmitate: esters of sorbitan and fatty acids such as, for example, lauric acid, palmitic acid and stearic acid; polyoxyethylenated esters of sorbitan and fatty acids containing from 4 to 20 moles of ethylene oxide per mole of ester: polyoxyethylenated fatty alcohols containing from 2 to 23 moles of ethylene oxide per mole of alcohol, it being preferred that said alcohol be lauryl alcohol, cetyl alcohol, stearyl alcohol or oleyl alcohol; glycerol mono- and distearate, glycerol mono- and dioleate; polyoxyethylenated fatty acids and, in particular, the polyoxyethylenated stearate containing from 18 to 100 moles of ethylene oxide per mole of acid,
- (c) an agent which permits adjusting the consistency, which may be a fatty alcohol or a fatty acid and preferably cetyl alcohol, stearyl alcohol or stearic acid.

In respect of the hydrophilic phase, same comprises water, preferably distilled, and various additives, especially:
- (a) a humidifying agent, for example propylene glycol, glycerol or sorbitol,
- (b) a preservative and more particularly o-phenylphenol and the following acids, their salts (Na, K, NH$_4$) or their esters having from 1 to 4 carbon atoms: benzoic acid, salicylic acid, sorbic acid or phydroxybenzoic acid,
- (c) a stabilizing agent, especially cellulose derivatives such as carboxymethyl cellulose and xanthan gum.

One illustration of a foundation formulation is the following:

| | | |
|---|---|---|
| (i) | liquid paraffin | 15% by weight |
| (ii) | glycerol mono- and distearate | 4% by weight |
| (iii) | cetyl alcohol | 1% by weight |

| | | |
|---|---|---|
| (i) | distilled water q.s. | 100% by weight |
| (ii) | propylene glycol | 3% by weight |
| (iii) | methyl para-hydroxybenzoate | 0.05% by weight |
| (iv) | propyl para-hydroxybenzoate | 0.1% by weight |
| (v) | colored pigment | 1 to 10% by weight |
| (vi) | titanium dioxide | 3% by weight |

The preparation of the foundation formulations is carried out by first dispersing the pigment in the lipophilic phase maintained at about 60°–80° C., and the hydrophilic phase, which is maintained at a temperature within the aforementioned interval, is then added slowly, and with stirring, to the lipophilic phase.

In the above description, examples of formulations intended for cosmetics in which the compositions or pigments of the invention are suitable are given, these being for purposes of illustration only.

In order to further illustrate the present invention and the advantages thereof, the following specific examples are given, it being understood that same are intended only as illustrative and in nowise limitative.

Said examples to follow illustrate not only the synthesis and characterization of certain of the supports and resulting compositions in accordance with the invention, but also their applications in the fields of coloration of plastics and in cosmetics.

EXAMPLE 1

This example illustrates the preparation of a cubic $\gamma$-Ce$_2$S$_3$ cerium sesquisulfide doped with sodium.

58 g of cerium oxalate Ce$_2$(C$_2$O$_4$)$_3$•2H$_2$O, 48 g of elemental sulfur and 2.2 g of anhydrous sodium carbonate were introduced into a mortar; the initial molar ratio Na/Ce in the mixture was then 0.20.

The mixture was then ground to provide a very homogeneous mixture.

This mixture was subsequently placed in a carbon crucible which was introduced into an airtight tubular oven. This oven was purged and then continuously flushed with argon charged with 10% of hydrogen.

The oven temperature was increased to 325° C. at a rate of 5° C./min, with a one hour holding period at this temperature.

The temperature was then increased to 1,100° C., also at a rate of 5° C./min, with a further holding period of four hours at this temperature.

The temperature is subsequently decreased to room temperature, the cooling being effected at a rate of 5° C./min.

The product recovered was subsequently washed once with deionized water.

The product obtained then had a very intense red color.

X-ray diffraction analysis evidenced that the cubic γ-$Ce_2S_3$ phase was obtained alone, with a lattice constant equal to 8.637 Å.

The sodium content of the product was 2.25% by weight (Na/$Ce_2S_3$).

Its chromatic coordinates were the following:
L* = 48
a* = 47
b* = 36

After simple deagglomeration (slightly forced grinding, air jet type) of the product, a powder having a mean particle diameter ($f_{50}$) of 2.5 μm (measured by a CILAS laser granulometer) was obtained.

Two tests were subsequently performed on this product, one of thermal stability, the other of chemical stability in an acid medium.

The thermal stability was evaluated using a test based on the determination of the temperature for recommencement of weight gain in TGA analysis (temperature increase of 6° C./min and with air flushing).

The chemical stability test was carried out in 0.5 N hydrochloric acid solution (acid of density 1.18, diluted to 5% in water).

Thus, by analysis of the TGA curve, it was observed that the breakdown in the thermal stability of the product began at 260° C.

Similarly, it was observed that the product dissolved instantaneously in the hydrochloric acid solution described above.

EXAMPLE 2

This example illustrates the preparation of a composite pigment $Ce_2S_3$(core)/$SiO_2$ (envelope/sheath) from the cerium sulfide prepared in Example 1.

The amounts and the nature of the reactants employed were the following (per kg of total mixture):

| (i) | Sodium-doped cerium sulfide | 53.29 g/kg |
|---|---|---|
| (ii) | 33% aqueous ammonia solution | 114.60 g/kg |
| (iii) | Tetraethyl orthosilicate | 44.34 g/kg |
| (iv) | Butanol | 787.77 g/kg |

The sodium-doped cerium sulfide was added to the aqueous/alcoholic ammonia solution and then dispersed in the latter by ultrasound. Ethyl silicate was subsequently added with stirring to the suspension of cerium sulfide particles obtained above. After reaction for two hours, the fresh particles obtained were recovered by centrifugation, and then washed twice with anhydrous ethanol. The washed particles were subsequently dried at 50° C. in an oven for 15 hours.

SEM analyses confirmed that composite particles comprising a sodium-doped cerium sulfide core coated with a layer of silica were obtained. Moreover, the electrophoretic mobility of these particles was identical to that of a pure silica.

The mean particle size (CILAS) of these composite particles was 5 μm ($f_{50}$).

Their trichromatic coordinates were the following:
L* = 45.5
a* = 49
b* = 39

According to the thermal stability test described above, it was observed that the weight gain of the product did not appear before 410° C.

Finally, there was a delay of 3 or 4 minutes before this product dissolved totally in the 0.5 N hydrochloric acid solution.

The latter two results indicate, on the one hand, a thermal stability and, on the other, a chemical stability of the compositions according to the invention which were clearly improved relative to the corresponding uncoated compositions.

The substantial improvement of the a* chromatic coordinate should also be noted.

EXAMPLE 3 (Comparative)

Example 1 of EP-A-0,203,838 was reproduced.

A cubic γ-$Ce_2S_3$ cerium sesquisulfide of red color was thus obtained, which product had the following trichromatic coordinates:
L* = 35
a* = 30
b* = 14

For a red color, these coordinates were plainly lower than those for the corresponding doped pigment prepared in Example 1, as well as those of the composite pigment prepared in Example 2.

In addition, this product dissolved instantaneously in the 0.5 N hydrochloric acid solution.

Finally, the thermal breakdown of the product, again according to the test defined above, was observed at 260° C.

EXAMPLE 4

This example illustrates the preparation of a cubic γ-$La_2S_3$ lanthanum sesquisulfide doped with potassium.

An initial mixture was thus prepared of:
(i) 59 g of lanthanum oxalate $La_2(C_2O_4)_3 \cdot 2H_2O$,
(ii) 48 g of elemental sulfur,
(iii) 4.24 g of anhydrous potassium carbonate.

The experimental procedure of Example 1 was subsequently repeated, with the sole difference that the final calcination step was carried out at 1,200° C. for one hour.

The final product obtained had a yellow color.

Its analysis by X-ray diffraction evidenced that the cubic γ-$La_2S_3$ phase was essentially obtained, with a few traces of $KLaS_2$.

Its potassium content was 4% by weight (K/$La_2S_3$).

The mean particle size of the product ($f_{50}$) was 3 μm (CILAS).

Its chromatic coordinates were the following:
L* = 80
a* = −3
b* = 46

According to the test defined above, the thermal stability of the product did not exceed 270° C.

Moreover, this product dissolved instantaneously in the 0.5 N hydrochloric acid solution.

EXAMPLE 5

This example illustrates the preparation of a composite pigment La$_2$S$_3$(core)/SiO$_2$(shell) from the lanthanum sulfide obtained in Example 4.

The amounts and nature of the reactants used were the following (per kg of total mixture):

| | | |
|---|---|---|
| (i) | Potassium-doped lanthanum sulfide | 52.68 g/kg |
| (ii) | 32% aqueous ammonia solution | 113.26 g/kg |
| (iii) | Tetraethyl orthosilicate | 43.83 g/kg |
| (iv) | Butanol | 779.87 g/kg |

The process was subsequently continued according to the experimental procedure given in Example 2.

The SEM and TEM analyses confirmed that composite particles comprising a potassium-doped lanthanum sulfide core coated with a silica layer were obtained. Moreover, the electrophoretic mobility of these particles was identical to that of a pure silica.

The mean particle size (f$_{50}$) of these composite particles was 5 μm (CILAS).

Their trichromatic coordinates were identical to those of the lanthanum sulfide prepared in Example 4 and used here as the support.

The thermal stability of the product (as evaluated by the test defined above) was on the order of 410° C.

Moreover, there was a delay of 3 to 4 minutes before this product dissolved totally in the 0.5 N hydrochloric acid solution.

EXAMPLE 6 (Comparative)

Example 3 of EP-A-0,203,838 was reproduced. A cubic γ-La$_2$S$_3$ lanthanum sesquisulfide of yellow color was thus obtained, having the following trichromatic coordinates:

$L^\bullet = 70$
$a^\bullet = -5$
$b^\bullet = 39$

For a yellow color, the chromatic coordinates were plainly lower than those obtained for the corresponding doped pigment of Example 4, as well as those of the composite pigment of Example 5.

In addition, this product dissolved instantaneously in the 0.5 N hydrochloric acid solution.

Finally, the thermal breakdown of the product, again according to the test described above, was observed at 270° C.

EXAMPLE 7

This example illustrates the suitability of the compositions according to the invention for the coloration of plastics.

20 g of the red composite pigment prepared in Example 2 (sodium-doped Ce$_2$S$_3$ core/SiO$_2$ shell; f$_{50}$=5 μm; $L^\bullet=45.5$; $a^\bullet=49$; $b^\bullet=39$) were mixed into a rotating cube containing 2 kg of a reference polypropylene, Eltex P HV 001.

The mixture was subsequently extruded at 180° C. using a ZSK 30 twin-screw extruder (marketed by Werner and Pfleiderer).

The granules obtained were subsequently injection-molded at 220° C. using an Arburg 350-90-220 D injection press with a cycle time of 41 seconds.

The mold was maintained at the temperature of 35° C.

A parallelepipedic test sample of two thicknesses (2 mm and 4 mm) having a width of 49 mm and a length of 69 mm was thus obtained. This test sample had a very attractive and uniform red color.

The chromatic coordinates of this test sample, measured on the thick part thereof (4 mm), were thus the following:

$L^\bullet = 38$
$a^\bullet = 42.5$
$b^\bullet = 32.5$

EXAMPLE 8

This example illustrates the use of a product of the invention for the production of a lipstick.

The constituent elements of the lipstick were the following:

| CONSTITUENTS | % BY WEIGHT |
|---|---|
| A | |
| Silbione oil 70641 V 200 | 40.5 |
| B | |
| Beeswax | 7.5 |
| Carnauba wax | 3.5 |
| Ozocerite | 3.5 |
| Paraffin | 10.0 |
| Liquid paraffin | q.s. 100 |
| Capric/caprylic acid triglyceride (*) | 20.0 |
| C | |
| Pigments according to Example 2 | q.s. |
| Titanium dioxide | q.s. |

(*) MYRITOL 318 from HENKEL

The components of the mixture B were melted at a temperature of 85°±2° C. and then maintained in a thermostatted bath regulated at 60°±2° C.

The pigment and the titanium dioxide were blended with the SILBIONE oil; this mixture A–C was placed in a thermostatted bath (60°±2° C.).

The mixture B was subsequently added.

The entire mixture was poured into appropriate silicone mold.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A colorant/pigment composition which comprises composite core/sheath particulates, the cores of which comprising particles of at least one crystalline rare earth metal sesquisulfide having the formula M$_2$S$_3$ in which M is at least one lanthanide element having an atomic number of from 57 to 71, or yttrium, and said core particles having at least one alkali and/or alkaline earth metal dopant at least in part incorporated within the crystal lattice of said at least one crystalline rare earth metal sesquisulfide, and each sheath comprising a coating layer of at least one transparent oxide deposited onto the external face surfaces of said doped core particles.

2. The colorant/pigment composition as defined by claim 1, said at least one transparent oxide comprising silica, alumina, zirconia, zircon, titanium dioxide, a rare earth metal oxide, or mixture thereof.

3. The colorant/pigment composition as defined by claim 2, said at least one transparent oxide comprising silica.

4. The colorant/pigment composition as defined by claim 3, said at least one transparent oxide consisting essentially of silica.

5. The colorant/pigment composition as defined by claim 1, said at least one dopant being essentially completely incorporated within the crystal lattice of said at least one crystalline rare earth metal sesquisulfide.

6. The colorant/pigment composition as defined by claim 1, said at least one dopant being present in the cationic lacunae of the crystal lattice of said at least one rare earth metal sesquisulfide.

7. The colorant/pigment composition as defined by claim 1, wherein the molar amount of said at least one dopant constitutes at least 0.1% of the molar amount of element M in said at least one rare earth metal sesquisulfide.

8. The colorant/pigment composition as defined by claim 7, wherein the molar amount of said at least one dopant ranges from 5% to 50% of the molar amount of element M.

9. The colorant/pigment composition as defined by claim 1, said at least one dopant comprising an alkali metal.

10. The colorant/pigment composition as defined by claim 9, said alkali metal comprising sodium.

11. The colorant/pigment composition as defined by claim 1, said core particles comprising a $Th_3P_4$ crystalline phase.

12. The colorant/pigment composition as defined by claim 1, said core particles comprising a cubic $\gamma$-$Ce_2S_3$ cerium sesquisulfide.

13. The colorant/pigment composition as defined by claim 1, having a chromatic coordinate L* at least equal to 30.

14. The colorant/pigment composition as defined by claim 13, having a chromatic coordinate L* ranging from 30 to 60.

15. The colorant/pigment composition as defined by claim 13, having a chromatic coordinate a* at least equal to 30.

16. The colorant/pigment composition as defined by claim 15, having a chromatic coordinate a* ranging from 35 to 65.

17. The colorant/pigment composition as defined by claim 15, having a chromatic coordinate b* ranging from 0 to 40.

18. The colorant/pigment composition as defined by claim 1, having a mean particle size ranging from 1 to 5 $\mu$m.

19. The colorant/pigment composition as defined by claim 1, comprising cerium sesquisulfide core particles doped with sodium and coated with a homogeneous layer of transparent silica.

20. The colorant/pigment composition as defined by claim 1, said core particles having a mean particle diameter ranging from 0.2 to 5 $\mu$m.

21. The colorant/pigment composition as defined by claim 1, having the same coloration as said core particles.

22. The colorant/pigment composition as defined by claim 1, said coating layer having an essentially uniform and controlled thickness.

23. The colorant/pigment composition as defined by claim 1, exhibiting brown-to-red, yellow, green-yellow, yellow-brown, brown, brown-grey, brown-green or green-gold coloration.

24. A process for the preparation of the colorant/pigment composition as defined by claim 1, comprising (i) intimately contacting said core particles with a precursor of said at least one transparent oxide, (ii) whereby precipitating said at least one transparent oxide onto the external face surfaces of said core particles, and (iii) separating the resulting core/sheath particulates from the medium of precipitation.

25. The process as defined by claim 24, comprising precipitating via hydrolysis of an alcoholate precursor of said at least one transparent oxide.

26. The process as defined by claim 25, said alcoholate precursor comprising a silicon, aluminum, zirconium and/or rare earth metal alcoholate.

27. The process as defined by claim 24, comprising precipitating via reacting a soluble salt precursor with a base.

28. The process as defined by claim 27, said base comprising aqueous ammonia or ammonium hydroxide.

29. The process as defined by claim 27, said soluble salt precursor comprising a halide or nitrate.

30. The process as defined by claim 27, said soluble salt precursor comprising a salt of silicon, aluminum, zirconium, titanium and/or of a rare earth metal.

31. The process as defined by claim 27, comprising simultaneously introducing said soluble salt precursor and said base into a liquid suspension of said doped core particles.

32. The process as defined by claim 24, comprising precipitating via reacting a silicate or aluminate precursor with an acid.

33. The process as defined by claim 32, said acid comprising sulfuric, hydrochloric or nitric acid.

34. The process as defined by claim 32, comprising reacting an alkali metal silicate or aluminate.

35. The process as defined by claim 32, comprising simultaneously introducing said silicate or aluminate precursor, together with said acid, into a liquid suspension of said doped core particles.

36. The process as defined by claim 32, comprising introducing said acid into a solution of said silicate or aluminate precursor, said solution having said doped core particles suspended therein.

37. The process as defined by claim 24, comprising hydrolyzing a zirconium and silicon alcoholate in a liquid suspension of said doped core particles which also comprises sodium fluoride, and thence calcining the particulates thus obtained.

38. The colorant/pigment composition prepared by the process as defined by claim 24.

39. A colorant/pigment comprising the core/sheath particulates as defined by claim 1.

40. A pigmented substrate comprising the colorant/pigment composition as defined by claim 1.

41. The pigmented substrate as defined by claim 40, comprising a plastic, paint, stain, rubber, ceramic, glaze, paper, ink, cosmetic, dye, or coating.

* * * * *